(12) United States Patent
Li et al.

(10) Patent No.: US 8,846,940 B2
(45) Date of Patent: Sep. 30, 2014

(54) PLATINUM (II) DI (2-PYRAZOLYL) BENZENE CHLORIDE ANALOGS AND USES

(71) Applicant: Arizona Board of Regents for and on behalf of Arizona State University, Scottsdale, AZ (US)

(72) Inventors: Jian Li, Phoenix, AZ (US); Zixing Wang, Shanghai (CN)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/063,332

(22) Filed: Oct. 25, 2013

(65) Prior Publication Data

US 2014/0066628 A1 Mar. 6, 2014

Related U.S. Application Data

(62) Division of application No. 12/809,367, filed as application No. PCT/US2008/087847 on Dec. 19, 2008, now abandoned.

(60) Provisional application No. 61/016,155, filed on Dec. 21, 2007.

(51) Int. Cl.
*C07F 15/00* (2006.01)
*H01L 51/00* (2006.01)
*C09K 11/06* (2006.01)

(52) U.S. Cl.
CPC ...... *H01L 51/0087* (2013.01); *C09K 2211/185* (2013.01); *C09K 2211/1029* (2013.01); *C09K 11/06* (2013.01); *Y02B 20/181* (2013.01); *C09K 2211/1037* (2013.01); *C09K 2211/1007* (2013.01); *C09K 2211/1044* (2013.01); *C07F 15/0086* (2013.01)
USPC ........................................................ 548/103

(58) Field of Classification Search
CPC ................................................ C07F 15/0086
USPC ........................................................ 548/103
See application file for complete search history.

(56) References Cited

U.S. PATENT DOCUMENTS

| | | | |
|---|---|---|---|
| 7,026,480 B2 | 4/2006 | Che et al. | |
| 7,029,766 B2 | 4/2006 | Huo et al. | |
| 7,166,368 B2 | 1/2007 | Lecloux et al. | |
| 7,276,617 B2 | 10/2007 | Sotoyama et al. | |
| 2002/0189666 A1 | 12/2002 | Forrest et al. | |
| 2006/0093854 A1 | 5/2006 | Sotoyama et al. | |
| 2006/0094875 A1 | 5/2006 | Itoh et al. | |
| 2007/0111025 A1 | 5/2007 | Lennartz et al. | |
| 2007/0224447 A1 | 9/2007 | Sotoyama et al. | |
| 2008/0067925 A1 | 3/2008 | Oshiyama et al. | |
| 2008/0269491 A1 | 10/2008 | Jabbour et al. | |
| 2011/0028723 A1 | 2/2011 | Li et al. | |
| 2011/0301351 A1* | 12/2011 | Li et al. ............................. 546/4 |
| 2012/0205554 A1* | 8/2012 | Hollis et al. ............... 250/459.1 |
| 2013/0137870 A1 | 5/2013 | Li et al. | |

FOREIGN PATENT DOCUMENTS

| | | |
|---|---|---|
| JP | 2006282965 A | 10/2006 |
| JP | 2006114889 A | 4/2007 |
| JP | 2008069268 A | 3/2008 |
| WO | WO00/70655 | 11/2000 |
| WO | WO2004/039781 | 5/2004 |
| WO | WO2005/075600 | 8/2005 |
| WO | WO2005/103195 | 11/2005 |
| WO | WO2005/105746 A1 | 11/2005 |
| WO | WO2006/082742 A1 | 8/2006 |
| WO | WO2006/100888 | 9/2006 |
| WO | WO2009/086209 | 7/2009 |
| WO | WO2009/111299 | 9/2009 |

OTHER PUBLICATIONS

S. A. Willison et al, "A Luminescent Platinum(II) 2,6-Bis(N-pyrazolyl)pyridine Complex", Inorg. Chem. vol. 43, pp. 2548-2555, 2004.
J. M. Longmire et al, "Synthesis and X-ray Crystal Structures of Palladium(II) and Platinum(II) Complexes of the PCP-Type Chiral Tridentate Ligand", Organometallics, vol. 17, pp. 4374-4379, 1998.
V. Adamovich et al., "High efficiency single dopant white electrophosphorescent light emitting diodes", New J. Chem, vol. 26, pp. 1171-1178. 2002.
Del Cano et al, "Near-infrared electroluminescence based on perylenediimide-doped tris(8-quinolinolato) aluminum", Applied Physics Letters, 88, pp. 071117-1-071117-3, 2006.
B. Harrison et al., "Near-infrared electroluminescence from conjugated polymer/lanthanide porphyrin blends", Applied Physics Letter, vol. 79, No. 23, pp. 3770-3772, Dec. 3, 2001.
J. Kido et al., "Organo Lanthanide Metal Complexes for Electroluminescent Materials", Chem. Rev., vol. 102, pp. 2357-2368, 2002.
S. Lamansky et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312, 2001.
S. Lamansky et al., "Synthesis and Characterization of Phosphorescent Cyclometalated Iridium Complexes", Inorg. Chem., vol. 40, pp. 1704-1711, 2001.
X. Li et al., "Synthesis and properties of novel poly(p-phenylenevinylene) copolymers for near-infrared emitting diodes", European Polymer Journal, vol. 41, pp. 2923-2933, 2005.

(Continued)

*Primary Examiner* — Joseph Kosack
(74) *Attorney, Agent, or Firm* — Fish & Richardson P.C.

(57) ABSTRACT

Synthesis of platinum(II) di(2-pyrazolyl)benzene chloride and analogs includes forming a 1,3-di-substituted benzene including two aromatic five-membered heterocycles, and reacting the 1,3-di-substituted benzene with an acidic platinum-containing solution to form a luminescent platinum(II) complex. The luminescent platinum(II) complex is capable of emitting blue and white light and can be used as an emitter in a light emitting device.

11 Claims, 8 Drawing Sheets

(56) References Cited

OTHER PUBLICATIONS

P. Peumans et al., "Small molecular weight organic thin-film photodetectors and solar cells", Journal of Applied Physics, vol. 93, No. 7, pp. 3693-3723, Apr. 1, 2003.

Rand et al., Organic Double-Heterostructure Photovoltaic Cells Employing Thick Tris (acetylacetonato) ruthenium (III) Exciton-Blocking Layers, Advanced Materials vol. 17, pp. 2714-2718, 2005.

C.W. Tang, "Two-layer organic photovoltaic cell", Appl. Phys. Letters 48 (2), pp. 183-185, 1986).

Vanhelmont et al., "Synthesis, Crystal Structure, High-Resolution Optical Spectroscopy, and Extended Huckel Calculations for [Re(CO)4(thpy)] (thpy- 2-(2-Thienyl)pyridinate). Comparison with Related Cyclometalated Complexes", Inorg. Chem., vol. 36, pp. 5512-5517, 1997.

Williams et al., "Organic light-emitting diodes having exclusive near-infrared electrophosphorescence", Applied Physics Letters, vol. 89, pp. 083506 (3 pages), 2006.

Forrest et al., "Measuring the Efficiency of Organic Light-Emitting Devices", Advanced Materials, vol. 15, No. 13, pp. 1043-1048, 2003.

Cardenas et al., "Divergent Behavior of Palladium(II) and Platinum(II) in the Metalation of 1,2-Di(2-pyridyl) benzene," Organometallics 1999, 18, pp. 3337-3341.

Williams et al., "An Alternative Route to Highly Luminescent Platinum(II) Complexes," Inorg. Chem., 2003, 42, pp. 8609-8611.

Sanna et al., "Platinum complexes with N-N-C ligands. Synthesis, electrochemical and spectroscopic characteristics of platinum(II) and relevant electroreduced species," Inorganica Chimica Acta 305, 2000, pp. 189-205.

International Search Report and Written Opinion, PCT/US2008/087847, mailed Aug. 6, 2009, 12 pages.

International Search Report and Written Opinion, PCT/US2009/03544, mailed Oct. 19, 2009, 14 pages.

Develay et al. "Cyclometalated Platinum(II) Complexes of Pyrazole-Based, N^C^N-Coordinating, Terdentate Ligands: the Contrasting Influence of Pyrazolyl and Pyridyl Rings on Luminescence" Inorganic Chemistry, vol. 47, No. 23, 2008, pp. 11129-11142.

Ionkin, A.S. et al.: Synthesis and structural characterization of a series of novel polyaromatic ligands containing pyrene and related biscyclometalated iridium complexes. Organometallics, vol. 25, pp. 1461-1471, 2006.

* cited by examiner

PLATINUM (II) DI (2-PYRAZOLYL) BENZENE CHLORIDE ANALOGS AND USES

PRIORITY CLAIM AND RELATED PATENT APPLICATION

This document is a divisional of U.S. patent application Ser. No. 12/809,367 entitled "Platinum(II) Di(2-Pyrazolyl) Benzene Chloride Analogs and Uses" and filed on Aug. 17, 2011, which is a §371 National Stage Application of International Appl. No. PCT/US2008/087847 entitled "Compositions and fabrication of Platinum (II) di(2-Pyrazolyl) Benzene Chloride or Their Analogs" and filed on Dec. 19, 2008, which claims priority from U.S. Provisional Patent Application Ser. No. 61/016,155 entitled "Platinum(II) Di(2-Pyrazolyl) Benzene Chloride Analogs and Uses" and filed on Dec. 21, 2007, the entire contents of all of which are incorporated herein by reference as part of the disclosure of this document.

TECHNICAL FIELD

This invention relates to platinum(II) di(2-pyrazolyl)benzene chloride and analogs, and more particularly to the synthesis and use thereof.

BACKGROUND

As depicted in FIG. 1, an organic light-emitting device (OLED) 100 may include a layer of indium tin oxide (ITO) as an anode 102, a layer of hole-transporting materials (HTL) 104, a layer of emissive materials (EML) 106 including emitter(s) and host(s), a layer of electron-transporting materials (ETL) 108, and a metal cathode layer 110 on substrate 112. The emission color of OLED 100 may be determined by the emission energy (optical energy gap) of the emitter(s) in the layer of emissive materials. Phosphorescent OLEDs (i.e., OLEDs with phosphorescent emitters) may have higher device efficiency than fluorescent OLEDs (i.e., OLEDs with fluorescent emitters). Some emitters for blue phosphorescent OLEDs include iridium—a relatively scarce element—in the form of cyclometalated iridium complexes.

SUMMARY

In one aspect, a luminescent compound has the generic formula

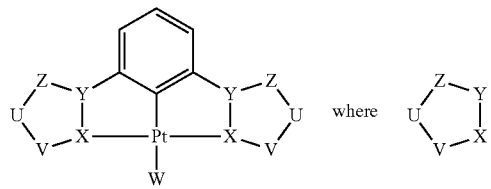

is an aromatic heterocycle
and where W is —Cl or

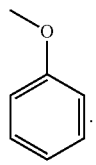

The six-membered ring in this generic formula denotes benzene or pyridine.

In another aspect, a light emitting device includes the luminescent compound shown above.

In certain implementations,

is selected from the group consisting of

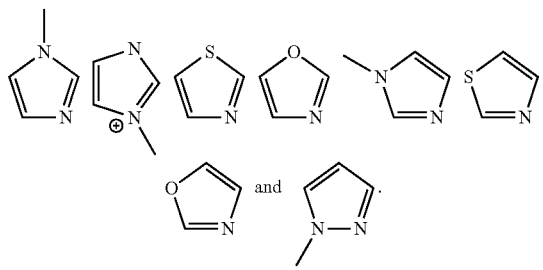

In certain implementations, the luminescent compound is platinum(II) di(2-pyrazolyl)benzene chloride, with the formula:

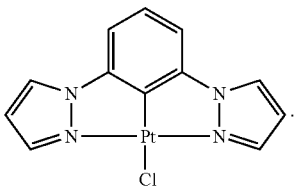

In some implementations, the luminescent compound is phosphorescent. The compound is capable of emitting light in the blue range of the visible spectrum. In some cases, the compound is capable of emitting white light. The light emitting device may be an organic light emitting device.

In another aspect, a method of making a platinum(II) complex includes forming a 1,3-di-substituted aromatic six-membered ring with two aromatic five-membered heterocycles, and reacting the 1,3-di-substituted six-membered ring with an acidic platinum-containing solution to form the platinum (II) complex.

In some implementations, the aromatic five-membered heterocycles are selected from the group consisting of pyrazolyl, substituted pyrazolyl, imidazolyl, substituted imidazolyl, thiazolyl, and substituted thiazolyl. In certain implementations, the benzene is fluorinated, difluorinated, or methylated. Fluorinating the benzene ring may increase the emission energy, shifting the emission toward the blue end of the visible spectrum. The benzene may be bonded to a heteroatom, such as a nitrogen atom or a sulfur atom, in the heterocycle. The platinum atom in the platinum(II) complex may be bonded to a carbon atom and two nitrogen atoms. In some embodiments, the platinum(II) complex is platinum(II) di(2-pyrazolyl)benzene chloride. In certain implementations, the aromatic six-membered ring is benzene or pyridine. In some cases, when the six-membered ring is pyridine, an increase in the emission energy may result.

Phosphorescent blue OLEDs with the platinum complexes described herein as emitters can be produced at low cost and provide operationally stable displays.

The details of one or more embodiments of the invention are set forth in the accompanying drawings and the description below. Other features, objects, and advantages of the invention will be apparent from the description and drawings, and from the claims.

DETAILED DESCRIPTION

The platinum complexes described herein can be used as emitters for OLEDs, absorbers for solar cells, luminescent labels for bio-applications, and the like. Blue phosphorescent OLEDs may include platinum complexes with high band-gap ligands, including the five-membered rings depicted herein.

Platinum(II) di(2-pyrazolyl)benzene chloride and analogs may be represented as:

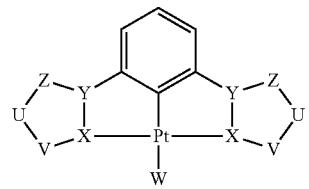

in which:

is an aromatic heterocycle,
and W can be —Cl or

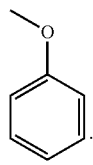

The aromatic six-membered ring in this generic formula denotes benzene or pyridine. The aromatic five-membered heterocycle can be, for example, substituted pyrazolyl, imidazolyl, substituted imidazolyl, thiazolyl, and substituted thiazolyl ligands shown below:

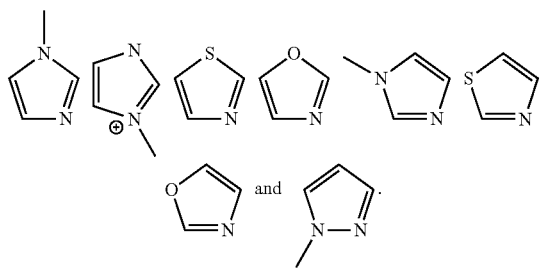

In some embodiments, the luminescent compound is platinum(II) di(2-pyrazolyl)benzene chloride, shown below:

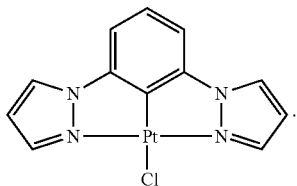

In some cases, the benzene ring is substituted, such as fluorinated or methylated in one or more positions. Fluorinating the benzene ring increases the emission energy, shifting the emission toward the blue end of the visible spectrum. In certain cases, the six-membered ring is a pyridyl ring rather than benzene.

Figure 1:
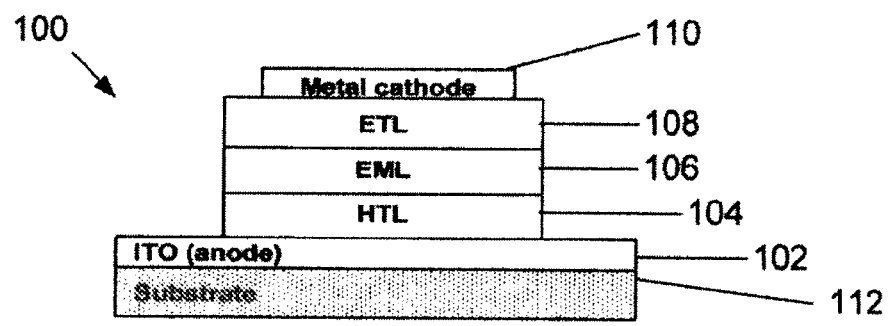
FIG. 1 illustrates an organic light emitting device (OLED).
Figure 2:
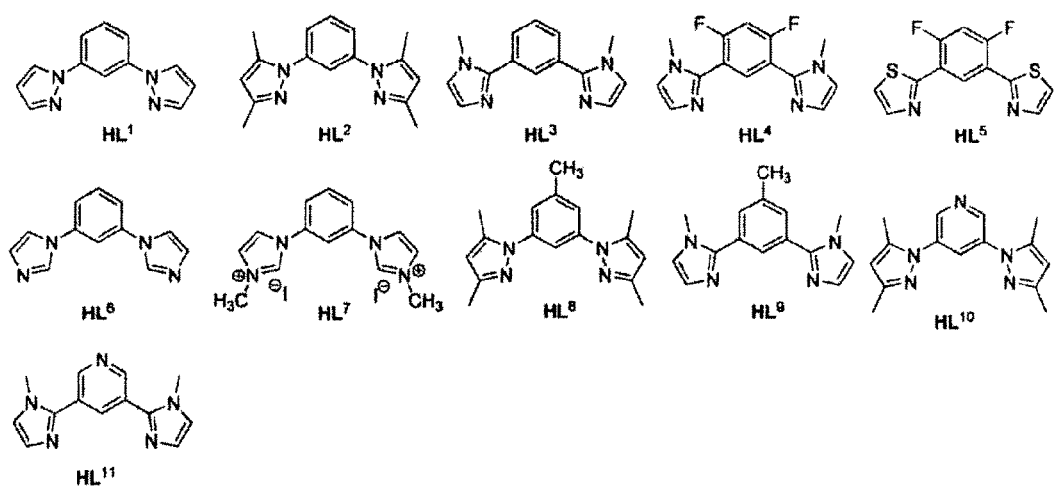
FIG. 2 shows precursors for platinum(II) di(2-pyrazolyl) benzene chloride and analogs.

Platinum(II) di(2-pyrazolyl)benzene chloride and analogs described herein may be prepared from the ligands depicted in FIG. 2. Synthesis of the ligands is described below.

$HL^1$: After standard cycles of evacuation and back-fill with dry and pure nitrogen, an oven-dried Schlenk flask equipped with a magnetic stir bar was charged with $Cu_2O$ (0.1 mmol, 10 mol %), syn-2-pyridinealdoxime (0.4 mmol, 20 mol %), the pyrazole (2.5 mmol), $Cs_2CO_3$ (5.0 mmol), and the 1,3-dibromobenzene (1.0 mmol), and anhydrous and degassed acetonitrile (20 mL). The flask was stirred in an oil bath, and refluxed for 3 days. The reaction mixture was allowed to cool to room temperature, diluted with dichloromethane and filtered through a plug of CELITE® (World Minerals Inc., Santa Barbara, Calif.), the filter cake being further washed with dichloromethane (20 mL). The filtrate was concentrated under vacuo to yield a residue, which was purified by flash column chromatography on silica gel to obtain the pure product $HL^1$ in 80% yield. $^1H$ NMR ($CDCl_3$): 6.51 (dd, 2H), 7.52 (t, 1H), 7.62 (dd, 2H), 7.76 (d, 2H), 8.02 (d, 2H), 8.10 (s, 1H).

$HL^2$: $HL^2$ was synthesized in 64% yield using the same procedure as $HL^1$ except that 1,3-diiodobenzene was used as starting material. $^1H$ NMR ($CDCl_3$): 2.6 (s 12H), 6.0 (s, 2H), 7.42 (dd, 2H), 7.51 (t, 2H), 7.55 (t, 2H).

$HL^3$: 1,3-bis(4,4,5,5-tetramethyl-1,3,2-dioxaborolan-2-yl)benzene (1.0 mmol), $Pd(OAc)_2$ (0.05 equiv), $PPh_3$ (0.2 equiv), 1-methyl-2-iodoimidazole (2.5 mmol) were resolved in dimethoxyethane/2M $K_2CO_3$ aqueous solution (20 mL, 1:1) under nitrogen atmosphere. The mixture was heated and refluxed for 24 h. After being cooled to room temperature, the reaction mixture was diluted with EtOAc, and poured into a brine solution. The organic layer was separated, and washed with the water, dried, filtered, and the filtrate was concentrated under reduced pressure. The residue was purified by column chromatography on silica gel to obtain the pure product $HL^3$ in 34% yield. $^1H$ NMR ($CDCl_3$): 3.72 (s 6H), 7.12 (d, 2H), 7.47 (t, 1H), 7.48 (d, 2H), 7.56 (s, 1H), 7.72 (d, 2H).

$HL^4$: $HL^4$ was synthesized in 40% yield using the same procedure as $HL^3$ except that 1,3-difluoro-4,6-bis(4,4,5,5-tetramethyl-1,3,2-dioxaborolan-2-yl)benzene was used as starting material instead of 1,3-bis(4,4,5,5-tetramethyl-1,3,2-dioxaborolan-2-yl)-benzene. $^1H$ NMR ($CDCl_3$): 3.63 (s, 6H), 7.09 (t, 1H), 7.13 (d, 2H), 7.35 (t, 1H), 7.60 (d, 2H).

$HL^5$: $HL^5$ was synthesized in 25% yield using the same procedure as $HL^3$ except that 2-bromothiozole was used as starting material instead of 1-methyl-2-iodoimidazole. $^1H$ NMR ($CDCl_3$): 7.13 (t, 1H), 7.49 (d, 2H), 7.98 (d, 2H), 9.23 (t, 1H).

$HL^6$: $HL^6$ was synthesized in 65% yield using the same procedure as $HL^1$ except that imidazole was used as starting material. $^1H$ NMR (DMSO): 7.26 (2H), 7.34 (2H), 7.41 (1H), 7.43 (2H), 7.62 (1H), 7.92 (2H).

$HL^7$: Methyl iodide (3 equiv) was syringed into a 50 mL round-bottomed flask charged with $HL^6$ (10 mmol) and DMSO (30 mL). The reaction was stirred under nitrogen in room temperature for 48 h. The mixture was poured into EtOAc (60 mL), and the white precipitate was formed, filtered, washed with ether, and air-dried to obtain $HL^7$ in 85% yield. $^1H$ NMR (DMSO): 3.99 (s, 6H), 7.97-8.00 (m, 3H), 8.00 (s, 2H), 8.31 (s, 1H), 8.37 (s, 2H), 9.89 (s, 2H).

$HL^8$: $HL^8$ was synthesized in 60% yield using the same procedure as $HL^1$ except that 1,3-diiodotoluene was used as starting material. $^1H$ NMR ($CDCl_3$): 2.28 (s, 6H), 2.32 (s, 6H), 2.44 (s, 3H), 5.98 (s, 2H), 7.26-7.28 (m, 3H).

$HL^9$: A mixture of 3,5-diiodotoluene (1.1 g, 3.0 mmol), 1-methylimidazole (7.5 mmol), $Pd(OAc)_2$ (5 mg, 0.01 mmol), KI (2.0 g, 12 mmol), and CuI (2.4 g, 12.2 mmol) in degassed DMF (12 mL) was heated under Ar at 140° C. for 10 days. After cooling to room temperature, the mixture was poured into $NH_3$ solution (10%, 50 mL), and $CH_2Cl_2$ (40×3 mL) was added. The organic phase was separated and dried ($MgSO_4$), and the solvent was evaporated. The crude product was purified by chromatograph (silica gel; ethyl acetate/methanol, 4:1) to give ligand $HL^9$ as a light yellow solid (40%). $^1H$ NMR ($CDCl_3$): δ2.44 (s, 3H), 3.78 (s, 6H), 6.97 (d, 2H), 7.11 (d, 2H), 7.52 (s, 2H), 7.60 (s, 1H).

$HL^{10}$: $HL^{10}$ was synthesized in 35% yield using the same procedure as $HL^1$ except that 1,3-dibromopyridine was used as starting material. $^1H$ NMR ($CDCl_3$): 2.3 (s, 6H), 2.4 (s, 6H), 6.06 (s, 2H), 8.00 (t, 1H), 8.71 (d, 2H).

$HL^{11}$: $HL^{11}$ was synthesized in 35% yield using the same procedure as $HL^9$ except that 1,3-dibromopyridine was used as starting material.

Pyridine-containing structures may be similarly synthesized.

Platinum(II) complexes were prepared from $HL^1$-$HL^{11}$ as described below.

Acetic acid (3 mL) and water (0.3 mL) were added to a mixture of the ligand $HL^n$ (e.g., 1.0 mmol) and $K_2PtCl_4$ (1 equiv) in a glass vessel with a magnetic stir bar. The vessel was capped, and then the mixture was heated under microwave irradiation for 30-60 minutes. Upon cooling to room temperature, a yellow or yellow-orange precipitate was formed. The precipitate was separated off from the yellow solution, washed sequentially with methanol, water, ethanol, and diethyl ether (e.g., 3×5 mL of each), and dried under vacuum.

Platinum (II) Ligand chloride ($PtL^{1-11}Cl$) were treated with phenol and potassium hydroxide in acetone to give $PtL^1$-$_{11}OPh$ for 2-3 hs after being filtrated, washed by water, acetone, and ether.

Figure 3:
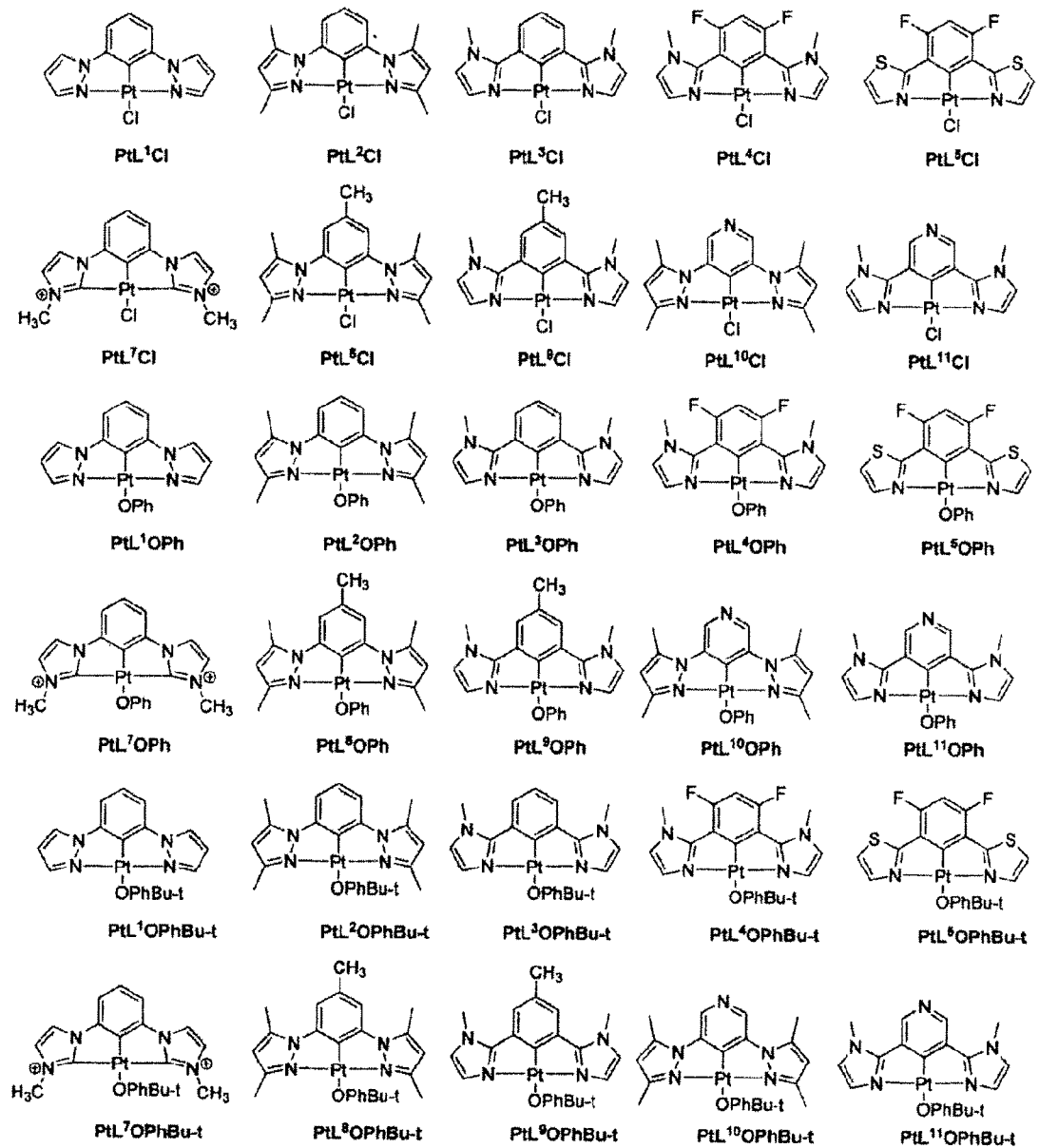
FIG. 3 shows platinum(II) di(2-pyrazolyl)benzene and analogs.

FIG. 3 shows platinum(II) di(2-pyrazolyl)benzene chloride and analogs synthesized from the ligands. $^1H$ NMR data for these compounds in DMSO or $CDCl_3$ are listed below.

$PtL^1Cl$: $^1H$ NMR (DMSO): 6.84 (dd, 2H), 7.37 (t, 1H), 7.48 (d, 2H), 7.93 (d, 2H), 8.91 (d, 2H).

$PtL^2Cl$: $^1H$ NMR (DMSO): 2.62 (s, 6H), 2.72 (s, 6H), 6.32 (s, 2H), 7.19-7.20 (m, 3H).

$PtL^3Cl$: $^1H$ NMR ($CDCl_3$): 7.40 (dd, 2H), 7.28 (d, 2H), 7.13 (t, 1H), 6.93 (d, 2H).

$PtL^5Cl$: $^1H$ NMR (DMSO): 7.28 (t, 1H), 7.95 (d, 2H), 8.14 (d, 2H).

$PtL^8Cl$: $^1H$ NMR ($CDCl_3$): 2.65 (s, 6H), 2.76 (s, 6H), 6.34 (s, 2H), 7.09 (s, 2H).

$PtL^9Cl$: $^1H$ NMR ($CDCl_3$): 7.37 (dd, 2H), 7.11 (d, 2H), 6.91 (d, 2H), 4.04 (s, 6H), 2.34 (s, 3H).

$PtL^{10}Cl$: $^1H$ NMR ($CDCl_3$): δ2.78 (s, 6H), 2.79 (s, 6H), 6.11 (s, 2H), 8.27 (s, 2H).

$PtL^2OPh$: $^1H$ NMR ($CDCl_3$): 7.07-7.16 (m, 5H), 7.02 (d, 2H), 6.49 (t, 1h), 6.01 (s, 2H), 2.71 (s, 6H), 2.45 (s, 6H).

$PtL^2OPhBu$-t: $^1H$ NMR ($CDCl_3$): 7.13 (t, 1H), 7.08 (d, 2H), 7.02 (d, 2H), 7.00 (d, 2H), 6.00 (s, 2H), 2.71 (s, 6H), 2.47 (s, 6H), 1.25 (s, 9H).

$PtL^3OPh$: $^1H$ NMR ($CDCl_3$): 7.23 (d, 2H), 7.17 (d, 2H), 7.11 (t, 1H), 7.06 (t, 1H), 6.85-6.87 (m, 4H), 6.78 (d, 2H), 3.99 (s, 6H).

FIGS. 4-12 show photoluminescence spectra for several Pt complexes including $PtL^1Cl$, $PtL^2Cl$, $PtL^3Cl$, $PtL^5Cl$, $PtL^8Cl$, $PtL^9Cl$, $PtL^{11}Cl$ and $PtL^2OPh$.

Figure 4:
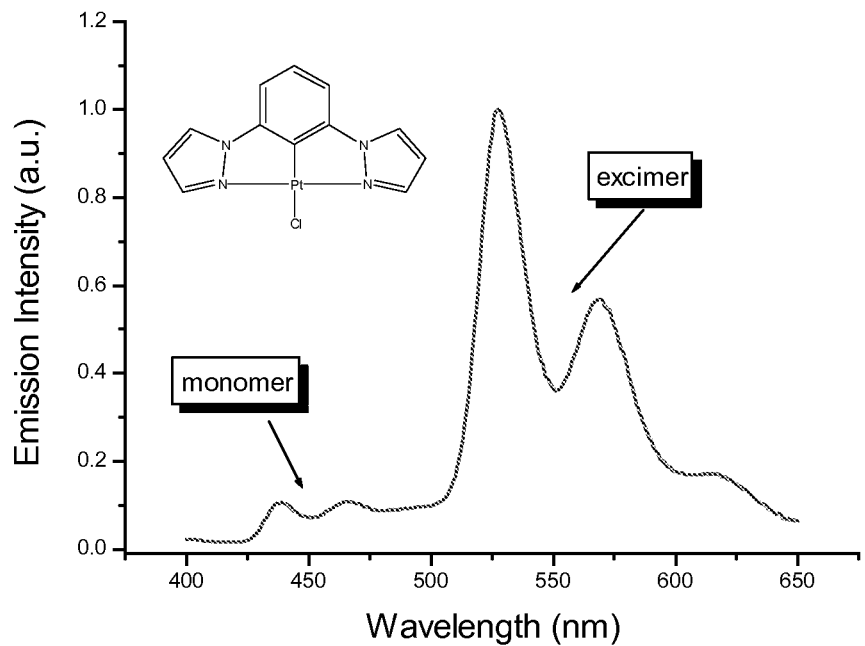
FIG. 4 shows a room temperature emission spectrum of platinum(II) di(2-pyrazolyl)benzene chloride in dichloromethane.

FIG. 4 shows a room temperature emission spectrum of platinum(II) di(2-pyrazolyl)benzene chloride in dichloromethane.

Figure 5:
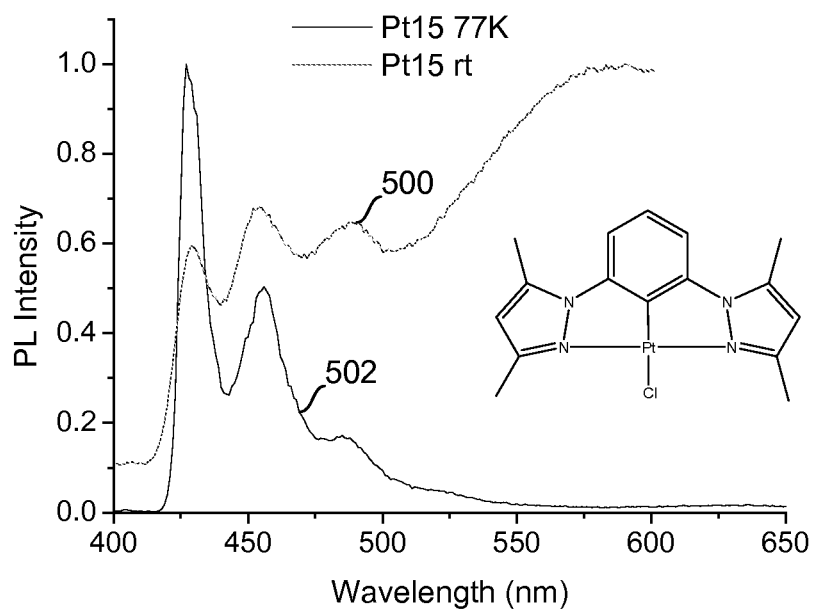
FIG. 5 shows room temperature and 77K emission spectra of platinum(II) di(3,5-dimethyl-2-pyrazolyl)benzene chloride in solution.

FIG. 5 shows room temperature (plot 500) and 77K (plot 502) emission spectra of platinum(II) di(3,5-dimethyl-2-pyrazolyl)benzene chloride in solution.

Figure 6:
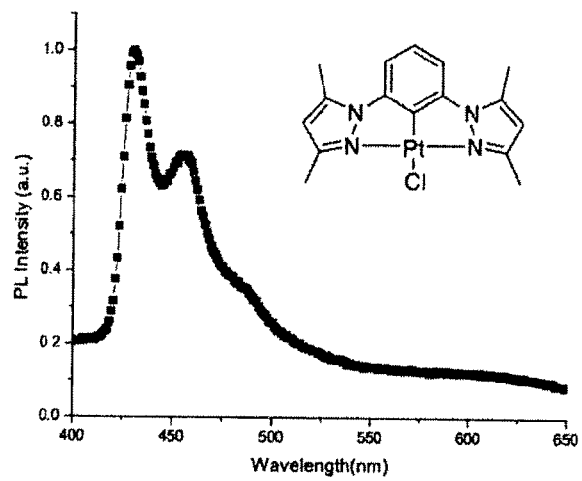
FIG. 6 shows a room temperature emission spectrum of platinum(II) di(3,5-dimethyl-2-pyrazolyl)benzene chloride in thin film of poly(methyl methacrylate) (PMMA).

FIG. 6 shows a room temperature emission spectrum of platinum(II) di(3,5-dimethyl-2-pyrazolyl)benzene chloride in thin film of poly(methyl methacrylate) (PMMA).

Figure 7:
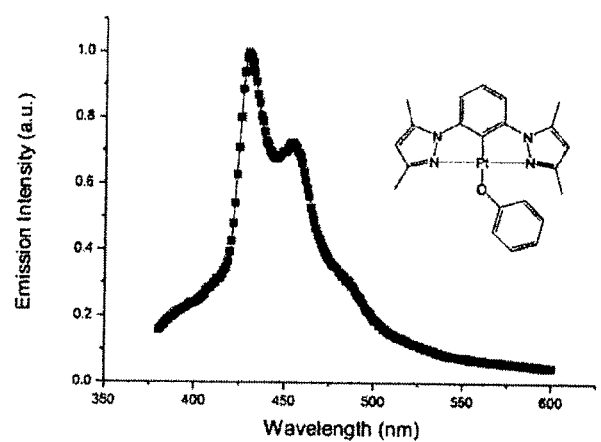
FIG. 7 shows a room temperature emission spectrum of platinum(II) di(3,5-dimethyl-2-pyrazolyl)benzene phenoxide in a thin film of poly(carbonate).

FIG. 7 shows a room temperature emission spectrum of platinum(II) di(3,5-dimethyl-2-pyrazolyl)benzene phenoxide in a thin film of poly(carbonate).

Figure 8:
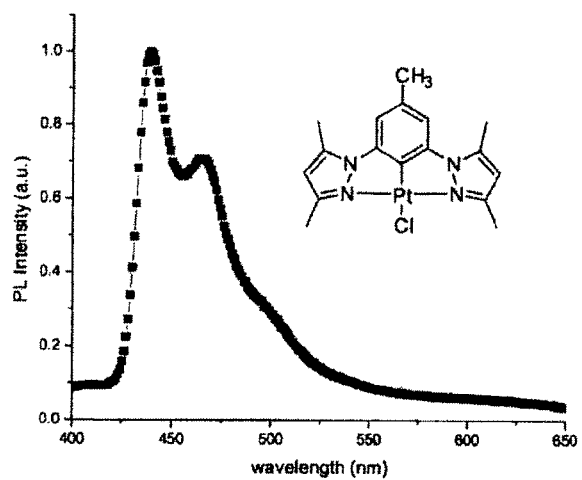
FIG. 8 shows a room temperature emission spectrum of platinum(II) di(3,5-dimethyl-2-pyrazolyl)toluene chloride in a thin film of poly(methyl methacrylate) (PMMA).

FIG. 8 shows a room temperature emission spectrum of platinum(II) di(3,5-dimethyl-2-pyrazolyl)toluene chloride in a thin film of poly(methyl methacrylate) (PMMA).

Figure 9:
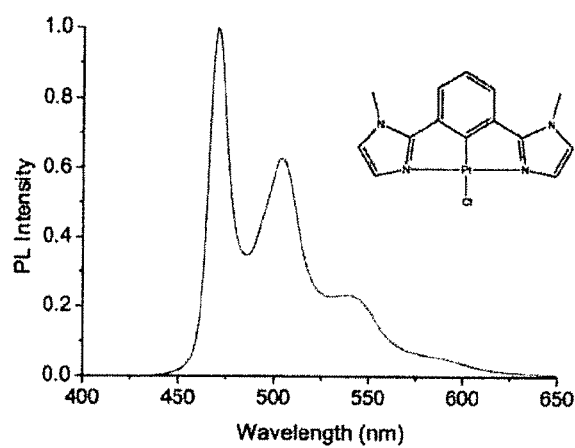
FIG. 9 shows a room temperature emission spectrum of platinum(II) di(methyl-imidazolyl)benzene chloride in a solution of dichloromethane.

FIG. 9 shows a room temperature emission spectrum of platinum(II) di(methyl-imidazolyl)benzene chloride in a solution of dichloromethane.

Figure 10:
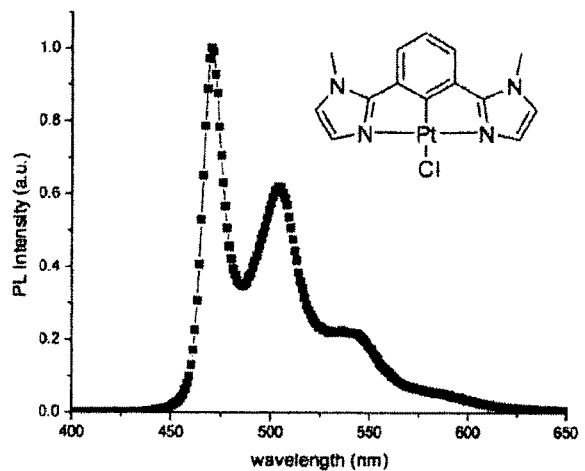
FIG. 10 shows a room temperature emission spectrum of platinum(II) di(methyl-imidazolyl)benzene chloride in a thin film of poly(methyl methacrylate) (PMMA).
Figure 11:
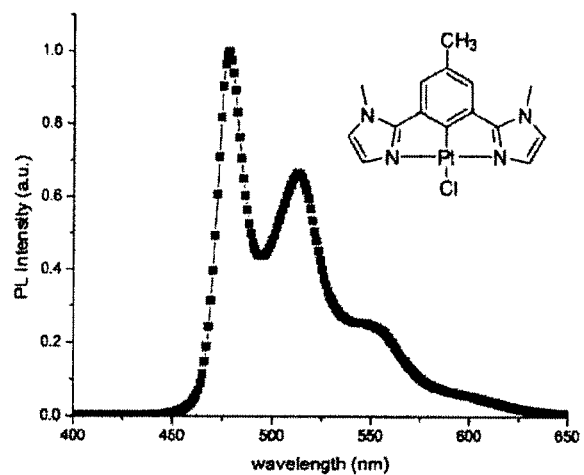
FIG. 11A shows a room temperature emission spectrum of platinum(II) di(methyl-imidazolyl)toluene chloride in a thin film of poly(methyl methacrylate) (PMMA).
FIG. 11B shows a 77K emission spectrum of platinum(II) di(methyl-imidazolyl)pyridine chloride in a solution of 2-methyl-tetrahydrofuran.
Figure 11:
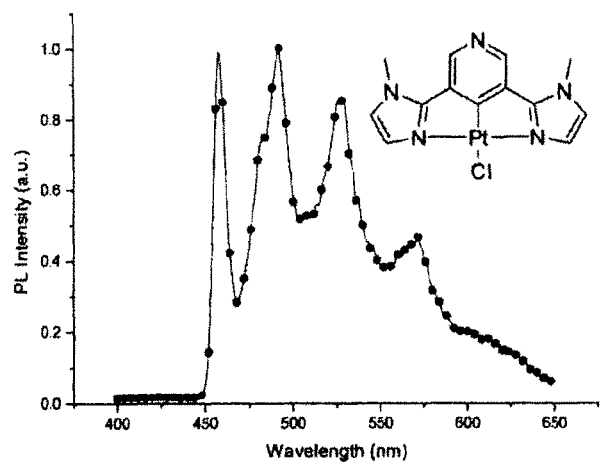

FIG. 10 shows a room temperature emission spectrum of platinum(II) di(methyl-imidazolyl)benzene chloride in a thin film of poly(methyl methacrylate) (PMMA).

FIG. 11A shows a room temperature emission spectrum of platinum(II) di(methyl-imidazolyl)toluene chloride in a thin film of poly(methyl methacrylate) (PMMA).

FIG. 11B shows a 77K emission spectrum of platinum(II) di(methyl-imidazolyl)pyridine chloride in a solution of 2-methyl-tetrahydrofuran.

Figure 12:
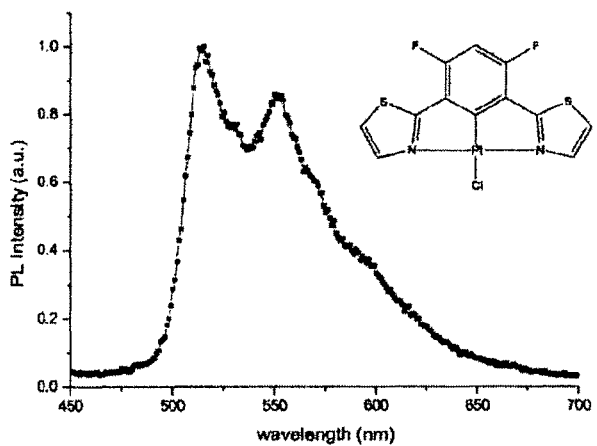
FIG. 12 shows a room temperature emission spectrum of platinum(II) di(thiazolyl)(4,6-difluoro-benzene) chloride in a solution of dichloromethane.

FIG. 12 shows a room temperature emission spectrum of platinum(II) di(thiazolyl)(4,6-difluoro-benzene) chloride in a solution of dichloromethane.

As seen in these spectra, these complexes provide the capability of tuning the emission energy of platinum(II) complexes over a range between ultraviolet and near-infrared, as well as improved emission in the blue wavelength range. These complexes can be used as luminescent labels, emitters for OLEDs, and other applications that benefit from efficient blue emission and high stability (longer lifetime).

A number of embodiments of the invention have been described. Nevertheless, it will be understood that various modifications may be made without departing from the spirit and scope of the invention.

What is claimed is:

1. A luminescent compound comprising:

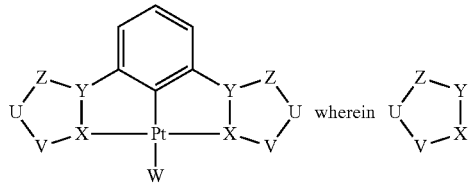

wherein is an imidazole ring, each X is a carbon atom, and W is —Cl or

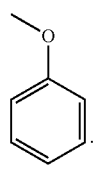

2. The compound of claim 1, wherein

is

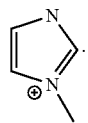

3. The compound of claim 1, wherein the compound is phosphorescent.

4. The compound of claim 1, wherein the compound emits light in the blue range of the visible spectrum.

5. The compound of claim 1, wherein the compound emits white light.

6. A light emitting device comprising a luminescent compound comprising:

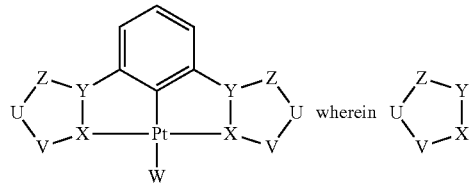

wherein is an imidazole ring, each X is a carbon atom, and W is —Cl or

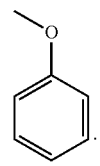

7. The light emitting device of claim 6, wherein

is

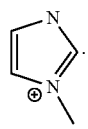

8. The device of claim 6, wherein the compound is phosphorescent.

9. The device of claim 6, wherein the compound emits light in the blue range of the visible spectrum.

10. The device of claim 6, wherein the compound emits white light.

11. The device of claim 6, wherein the device is an organic light emitting device.

* * * * *